(12) United States Patent
Gensinger et al.

(10) Patent No.: US 12,161,775 B2
(45) Date of Patent: Dec. 10, 2024

(54) STERILIZATION VALIDATION SYSTEM AND METHOD

(71) Applicant: Aramark Uniform & Career Apparel Group, Inc., Burbank, CA (US)

(72) Inventors: Daniel R. Gensinger, Scottsdale, AZ (US); Michael J. Rataj, Carol Stream, IL (US)

(73) Assignee: VESTIS GROUP, INC., Burbank, CA (US)

( * ) Notice: Subject to any disclaimer, the term of this patent is extended or adjusted under 35 U.S.C. 154(b) by 695 days.

(21) Appl. No.: 17/205,453

(22) Filed: Mar. 18, 2021

(65) Prior Publication Data

US 2022/0296759 A1   Sep. 22, 2022

(51) Int. Cl.

| | |
|---|---|
| *A61L 2/28* | (2006.01) |
| *A61L 2/18* | (2006.01) |
| *B08B 7/00* | (2006.01) |
| *B65B 55/18* | (2006.01) |
| *D06F 35/00* | (2006.01) |
| *D06F 95/00* | (2006.01) |
| *A61L 101/02* | (2006.01) |

(52) U.S. Cl.
CPC .............. *A61L 2/28* (2013.01); *A61L 2/186* (2013.01); *B08B 7/0021* (2013.01); *B65B 55/18* (2013.01); *D06F 35/00* (2013.01); *D06F 95/002* (2013.01); *A61L 2101/02* (2020.08); *A61L 2202/17* (2013.01); *A61L 2202/181* (2013.01); *A61L 2202/24* (2013.01); *A61L 2202/26* (2013.01)

(58) Field of Classification Search
CPC ......... A61L 2/186; A61L 2202/26; A61L 2/28
USPC ........................................... 53/425
See application file for complete search history.

(56) References Cited

U.S. PATENT DOCUMENTS

| 6,767,509 B1 * | 7/2004 | Griesbach ............... B65B 55/18 |
| | | 422/294 |
| 7,142,118 B2 * | 11/2006 | Hamilton ............. G06Q 10/087 |
| | | 377/5 |
| 2003/0170142 A1 | 9/2003 | Lepore |

(Continued)

FOREIGN PATENT DOCUMENTS

| CN | 103722809 A | 4/2014 |
| EP | 2467084 B1 | 6/2012 |

OTHER PUBLICATIONS

Tyvek® Sterilizing Bags, Thomas Scientific, https://www.thomassci.com/Laboratory-Supplies/Bags/_/Sterilization-Pouches?q=Sterilization%20Pouch.

(Continued)

*Primary Examiner* — Robert F Long
*Assistant Examiner* — Xavier A Madison
(74) *Attorney, Agent, or Firm* — Cozen O'Connor

(57) ABSTRACT

A sterilization validation system and method are disclosed that ensure sterilization of packaging materials that contain certain sterilized items that have been sterilized in a cleanroom environment. In accordance with the disclosed subject matter, garments (or other items or materials) that are sterilized inside autoclave or breather bags may be secured within tote liners that ensure sterility of the exterior of the breather bags containing the garments. Not only is it possible to ensure a recipient that the garment is sterile, but it is also possible to verify that the outside of the breather bag itself is also sterile, since the breather bag will remain sterilized inside the tote liner during shipping.

18 Claims, 3 Drawing Sheets

(56) References Cited

U.S. PATENT DOCUMENTS

2008/0240979 A1* 10/2008 Lin .......................... A61L 2/24
                                                           422/1
2016/0346416 A1* 12/2016 Schwartz ................. A61L 2/22
2018/0085482 A1*  3/2018 Rataj ....................... A61L 2/26
2020/0237945 A1    7/2020 Goforth
2020/0385778 A1* 12/2020 Witcher .................. C12Q 1/22

OTHER PUBLICATIONS

Sterilization Pouches, Spear Pack, https://spearpack.com/sterilization-pouches.html.

* cited by examiner

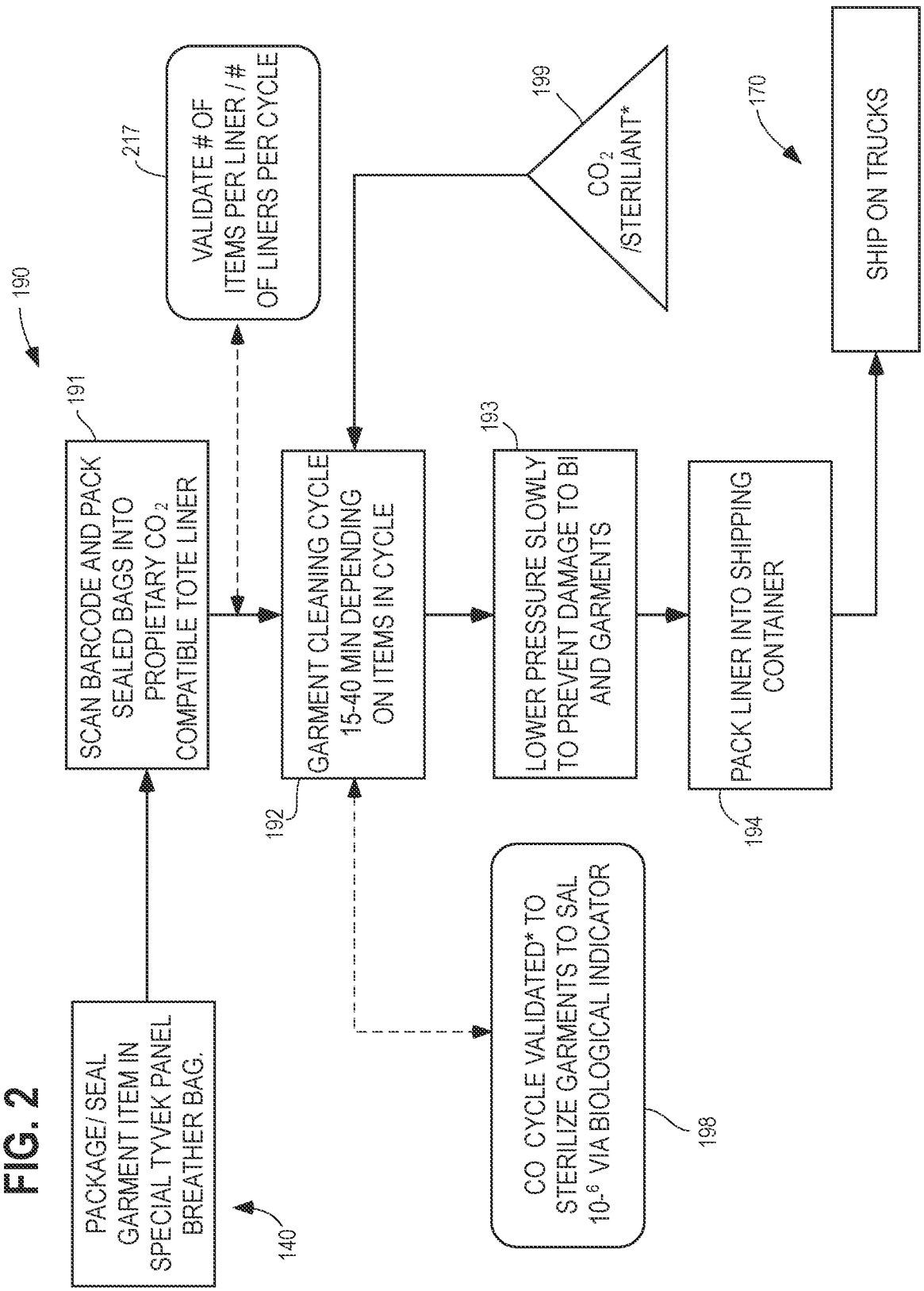

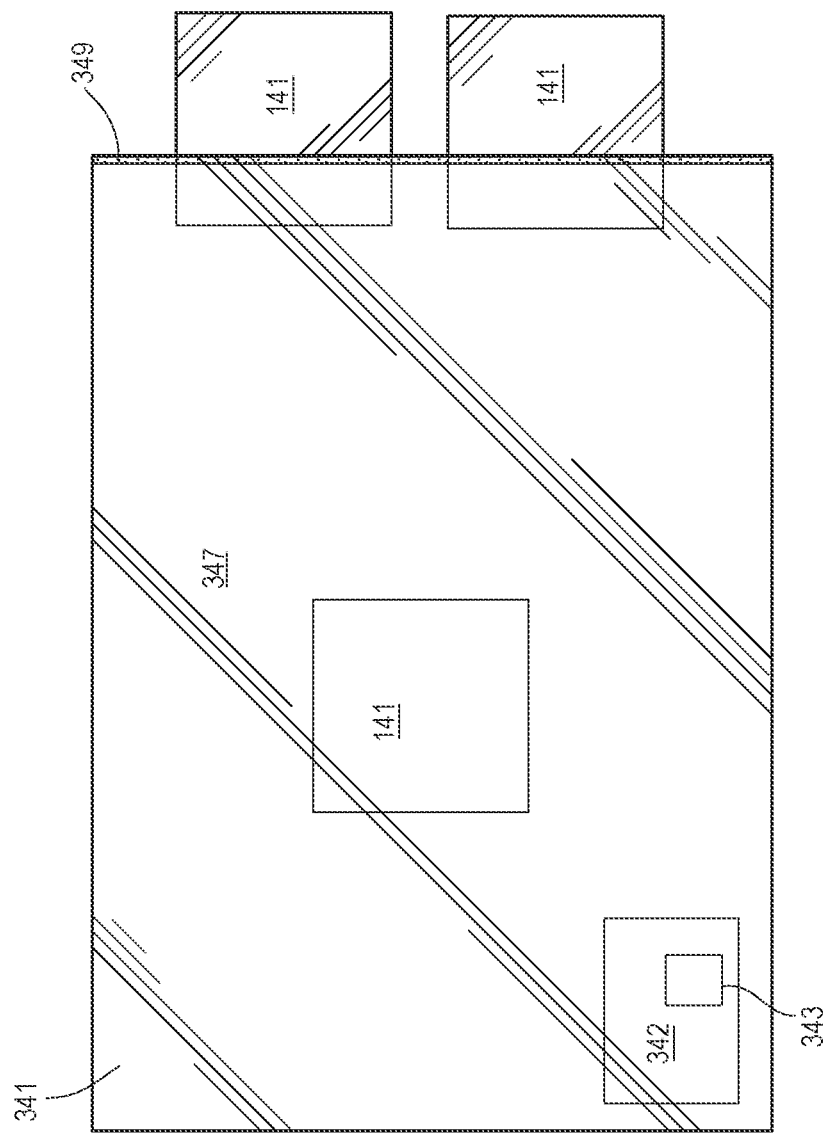

STERILIZATION VALIDATION SYSTEM AND METHOD

FIELD OF THE DISCLOSURE

Aspects of the disclosed subject matter relate generally to systems and methods for sterilizing items (such as garments and equipment) within a cleanroom setting, and more particularly to a sterilization validation system and method that ensures sterilization of packaging materials that contain the sterilized items.

BACKGROUND

Within a cleanroom setting (for example, in the manufacture, preparation, or handling of pharmaceuticals, food products, semiconductors, personal protective equipment (PPE), or biologically sensitive products or materials), it is often necessary to sterilize equipment used in the processing of those goods or materials, the garments worn by individuals handling those goods or materials, or both. The sterilization process is typically accomplished by inserting the equipment or garments to be sterilized into an autoclave bag, and then inserting the bag into an autoclave to be subjected to a high temperature, high pressure sterilization process. Traditionally, the equipment or garments are then preserved in the autoclave bag until needed.

In general, autoclave bags used for this purpose (sometimes referred to as "breather bags") are typically single-use products made from polyethylene, paper, TYVEK™ olefin material, such as that produced by E. I. du Pont de Nemours and Company of Wilmington, Del., or combinations of such materials, either with or without other suitable materials. The fact that these consumable bags are only used one time is wasteful and environmentally unsound. In some circumstances, equipment or instruments that are repeatedly placed in autoclave bags develop burrs during use or from successive autoclave cycles, or may have sharp edges by design. Such burrs or sharp edges may break through the seal of the polyethylene bag or cause the TYVEK™ or other material to particulate. Additionally, non-stock sized breather bags can be expensive to procure and have long lead times to produce, as they are typically only mass-produced and are not manufactured "to order" as needs arise.

Further, in accordance with conventional technologies, autoclave bags utilize draw strings or heat seals as closures, which may fail during use, or may otherwise be difficult to use or to open properly. Certain types of prior autoclave bags may comprise or be produced from plastic materials, such as polypropylene, that have a tendency to outgas when the bag is heated to the extreme temperatures and pressures needed to achieve sterility. This outgassing, which may be acceptable for use in connection with sterilization of certain equipment or instruments, may prove less than desirable in other situations.

In this context, U.S. Pat. No. 10,183,090 and related applications (U.S. patent application Ser. Nos. 16/213,062 and 17/152,607), all of which are owned by the assignee of the present application, disclose and claim an autoclave bag and hopper cover system featuring a breather bag that is puncture resistant and will not rip or tear when a sharp piece of equipment is placed within it. The disclosures of the foregoing patent and pending applications are hereby incorporated by reference in their entireties.

In some product fill lines or garment sterilization processing methodologies, it is often necessary to maintain the sterility of hoppers, bins, or other conveyance or shipping containers having an opening (allowing access to the sterilized items contained in the hopper), which is typically closed by some form of removable or moveable sterilized cover, lid, or other suitably sized and dimensioned panel. In a typical application, while the equipment, instruments, or garments inside the breather bag may be clean and sterile, there is no guaranty that the outside of the breather bag is also sterile, since the exterior of the breather bag is exposed to shipping environments after leaving the cleanroom, including the environment inside the hopper or bin. There is a need, therefore, for a system and method that can not only ensure a recipient that the equipment or garments are sterile, but also verify that the outside of the breather bag itself is also sterile (and remained so inside the hopper) upon receipt by such recipient.

SUMMARY OF THE DISCLOSURE

The following presents a simplified summary of the disclosure in order to provide a basic understanding of some aspects of various embodiments disclosed herein. This summary is not an extensive overview of the disclosure. It is intended neither to identify key or critical elements of the disclosed embodiments nor to delineate the scope of those embodiments. Its sole purpose is to present some concepts of the invention in a simplified form as a prelude to the more detailed description that is presented later.

The present disclosure describes a sterilization validation system and method that ensures sterilization of packaging materials that contain certain sterilized items that have been sterilized in a cleanroom environment. Examples are set forth below that are directed to garments, though other implementations may be directed to instruments, equipment, or other materials that are sterilized for later use after delivery to a recipient. Garments (or other items or materials) that are sterilized inside autoclave or breather bags may be secured within tote liners (as set forth below) that ensure sterility of the exterior of the breather bags containing the garments. In some implementations, not only is it possible to ensure a recipient that the garment is sterile, but it is also possible to verify that the outside of the breather bag itself is also sterile, since the breather bag will remain sterilized inside the tote liner during shipping.

In accordance with one aspect of the disclosed subject matter, for example, a sterilization validation method may generally comprise: loading a sealed breather bag containing a cleaned item into a $CO_2$ compatible tote liner, the tote liner comprising a $CO_2$ permeable sleeve and containing a biological indicator to indicate a level of sterility; sealing the tote liner and exposing the sealed tote liner to a cleaning cycle utilizing $CO_2$ and a sterilant; lowering a pressure following the cleaning cycle slowly to prevent damage to the biological indicator; confirming sterilization using the biological indictor; and packaging the sterilized tote liner into a container for shipping.

Methods are disclosed wherein the cleaned item is one of equipment, an instrument, a garment, and material. In some implementations, the exposing comprises utilizing a solution comprising between 15% and 30% weight to volume of hydrogen peroxide as the sterilant, though other ranges are possible, such as between 20% and 30%, or between 25% and 30%.

In some methods, the exposing comprises utilizing a high pressure, low temperature cleaning cycle, the temperature and pressure parameters of which may be adjusted independently as set forth below.

For example, methods are disclosed wherein the high pressure, low temperature cleaning cycle achieves a pressure of about 250 pounds per square inch (psi) to about 1000 psi inside a wash cylinder of a machine configured to execute the cleaning cycle; other pressure ranges may be appropriate, such as between about 500 psi to about 750 psi. Similarly, methods are disclosed wherein the high pressure, low temperature cleaning cycle achieves a temperature of about 0° Celsius to about 40° Celsius inside the wash cylinder, though narrower ranges are also disclosed.

In some methods, the lowering comprises lowering the pressure inside the wash cylinder at a rate of approximately 2 psi/sec to approximately 7 psi/sec; again, other ranges are contemplated.

In accordance with some implementations, the confirming comprises certifying that an exterior surface of the breather bag is sterile inside the tote liner; this may be achieved in some methods wherein the confirming comprises certifying the level of sterility to at least a Sterility Assurance Level of $10^{-6}$. One example includes a method wherein the biological indicator comprises *Bacillus atrophaeus*.

In accordance with another aspect of the disclosed subject matter, a tote liner for use in a sterilization validation method is disclosed, the tote liner generally comprising: a $CO_2$ permeable sleeve, the sleeve allowing liquid $CO_2$ and a sterilant to permeate a material of the sleeve during a pressurized cleaning cycle; and a biological indicator to indicate a level of sterility to at least a Sterility Assurance Level of $10^{-6}$.

Tote liners are disclosed wherein the biological indicator is contained in an interior space within the sleeve, and wherein the biological indicator is integrated into a structure of the sleeve. In some implementations, as noted above, the biological indicator comprises *Bacillus atrophaeus*.

Implementations are disclosed wherein the sterilant comprises a solution comprising between 15% and 30% weight to volume of hydrogen peroxide and wherein the sleeve is constructed of a material to allow the solution to permeate.

As set forth below, the sleeve may be sized and dimensioned to accommodate a breather bag containing a sterilized item (such as equipment, and instrument, or a garment). The disclosed tote liners may further comprise a sealing mechanism to prevent contamination of the breather bag; such a sealing mechanism may comprise a cleanroom compatible coil zipper designed to maintain sterility of the breather bag inside the sleeve.

The foregoing and other aspects of various disclosed embodiments will be apparent through examination of the following detailed description thereof in conjunction with the accompanying drawing figures, in which like reference numerals are used to represent like components throughout, unless otherwise noted.

DESCRIPTION OF THE DRAWING FIGURES

FIG. 2 is a simplified process flow diagram illustrating aspects of a method of validating sterilization of a garment, which aspects may be inserted into the process flow depicted in FIG. 1; and FIG. 3 is a simplified block diagram illustrating aspects of a tote liner for use in connection with a sterilization process.

DETAILED DESCRIPTION

Figure 1:
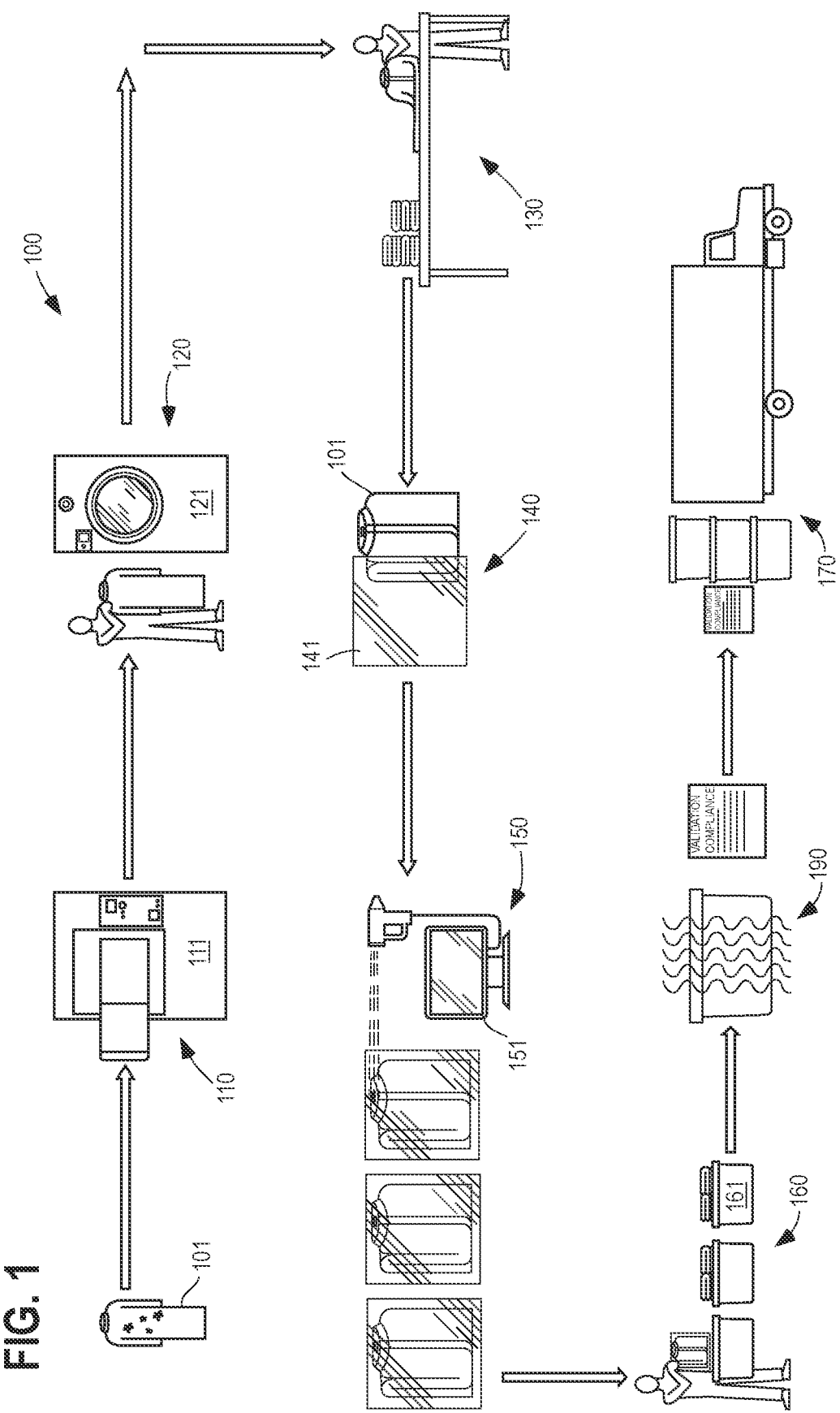
FIG. 1 is a simplified process flow diagram illustrating aspects of a method of sterilizing a garment.

Certain aspects and features of the disclosed subject matter may be further understood with reference to the following description and the appended drawing figures. In operation, a validation method or appropriate system components may be inserted into a sterilization process flow as set forth below.

In some instances, garments (or other items or materials) that are sterilized inside of autoclave or breather bags may be secured within tote liners that ensure sterility of the exterior of the breather bags containing the garments. In that regard, and as noted above, while certain example implementations described below are related specifically to garments or other protective wear, it will be appreciated that the disclosed subject matter may also be applicable to any other item (such as equipment, instruments, or other materials) that are typically sterilized in a cleanroom setting. In that regard, the term "garment" is used only as an example, and is intended to reference items, in general, that include medical, surgical, or dental instruments, protective gear (such as masks, aprons, laboratory coats, and goggles or other eye protection apparatus), tools or other equipment used in the semiconductor, nuclear, or biotechnology industries, or any other item the re-use of which requires or benefits from sterilization processes as set forth herein. Specifically, the present disclosure is not intended to be limited by the nature, construction, materials, fabrication methods, or operational characteristics of the items placed in the breather bags, irrespective of whether those items are referred to as "garments."

Similarly, the terms "autoclave bag" and "breather bag" are used interchangeably in this disclosure. In operation, such an autoclave or breather bag receives an item to be sterilized and is sealed with such item contained within, as is generally known in the art. Such a bag may be sized and dimensioned to receive more than one item (or even more than one type of item) during use. For example, a single breather bag may contain garments such as trousers and a shirt, a laboratory coat, protective eye wear, and booties or other shoe coverings, such that a single bag contains an entire sterilized outfit for one cleanroom or laboratory worker. Alternatively, a single breather bag may contain a plurality of similar items, such as laboratory coats or goggles, for example, depending upon the desires or the requirements of the facility receiving the sterilized items. The present disclosure is not intended to be limited by the number and type of items placed in a particular breather bag for sterilization as set forth below.

Turning now to the drawing figures, FIG. 1 is a simplified process flow diagram illustrating aspects of a method of sterilizing a garment. A sterilization process 100 typically begins with collection of a soiled garment 101 or other item. In a typical commercial setting, such as illustrated in process 100, such a soiled garment 101 or other items may be retrieved from a medical center, a semiconductor or pharmaceutical manufacturing operation, a nuclear plant, a laboratory, or some other facility requiring re-use of sterilized garments 101 or other equipment or materials. Items are then washed thoroughly as indicated at reference numeral 110. The cleaned garment 101 or other item then enters a cleanroom after washing, is dried (reference numeral 120), inspected (reference numeral 130), and packaged and sealed (reference numeral 140), typically in a breather bag 141 constructed of polyethylene, paper, or olefin material (such as TYVEK™). Upon scanning or other inventory control (reference numeral 150), breather bag 141 is (or a plurality of breather bags 141 are) packaged (reference numeral 160) prior to exiting the cleanroom environment for return to its origin or for delivery to a third party (reference numeral 170) for terminal sterility processing, which typically includes gamma irradiation, high temperature application of ethylene oxide, or both. Importantly, this terminal sterility processing must occur after shipping at reference numeral 170, since the breather bag 141 containing the sterile garment 101 or other item is, itself, subjected to an unsterile environment during shipping or after delivery at a destination.

In some implementations, the washing process at reference numeral 110 (and many of the other processing operations depicted in FIG. 1) may be standardized across many processing locations, and may be specifically designed and validated to produce garments 101 or other items that (at the point of shipment at reference numeral 170) meet the strict cleanliness requirements for the cleanroom, laboratory, or other facility that provided the garment 101 or other item to be sterilized. In that regard, the item handling procedures and wash cycles (such as at reference numerals 110 and 120) may also be validated to allow for the sterilization of garment 101 and other items via gamma irradiation, post-processing (as noted above). In practice, such standardized processes in commercial applications allow for each processing location or facility to serve as a backup or fail-safe facility for other processing locations or facilities in the case that any single plant, location, or facility suffers an unplanned interruption of service.

Typically, collection and handling procedures involving soiled garment 101 or other contaminated or "dirty" items may be designed and implemented to comply with or otherwise to follow industry-recognized precautions, policies, and procedures for the protection of employees who work in the "soil sort" and "wash aisle" areas (such as at reference numeral 110) of the cleaning facilities.

During the collection at a medical facility, semiconductor manufacturing plant, or the like, typically, each shipment of soil garments (such as garment 101) may generally receive or be associated with an individual customer, batch, or other reference number or identifier; in some implementations, this identification paradigm may include providing garment 101, either individually or in combination with a collection or batch of additional garments or other items, a unique lot number or other identifier that traces garment 101 throughout process 100. The specific processing methodologies required for garment 101 may be pre-determined, for example, responsive to a questionnaire or survey that is completed by a specific customer at the initiation of service with the sterilization facility operating process 100, or it may be selected upon collection of garment 101 or may otherwise be application-specific (for instance, as a function of the requirements for a particular garment 101 or batch). In operation, aspects of the individual processing operations in process 100 may be indicated or selectively adjusted by data or other information associated with the indicator or identifier associated with garment 101, as is typical in the art. This may allow an administrator controlling or monitoring process 100 to determine whether a garment is handled in accordance with desired protocols and whether there is a danger of garment 101 or other items creating a cross contamination risk in the plant or facility executing process 100.

The washing process at reference numeral 110 may use standardized water-based or other wash methods to clean garments 101 or other items for re-use in cleanrooms or for other sterile applications (such as in laboratories, medical facilities, and the like). In accordance with some implementations, the wash process operation at reference numeral 110 may be performed in one of various commercially available washing machines (one of which is depicted in FIG. 1 at reference numeral 111). In that regard, washing machine 111 may be any suitable type or model of washing machine as may be designed for the medical laundry market, the semiconductor laundry market, or other markets or industries having a need for sterilized garments and other items. These washing machines, such as machine 111, typically feature a pass-through load/unload product flow, which is suitable for the cleanroom laundry industry. As is generally known in the art, this feature allows for soiled garments to be loaded on the soil side (i.e., the left side of reference numeral 110) of machine 111 and unloaded on the sterile or cleanroom side (i.e., the right side of reference numeral 110) once the wash cycle has been completed. The present disclosure is not intended to be limited by any particular manufacturer, model, type, or specific operational characteristics of machine 111.

The efficacy of the wash process at 110 may generally depend upon control of several variables, which, as noted above, may be pre-determined for a particular customer or selected dynamically as a function of an identifier or other indicia associated with a specific garment 101 or other item to be sterilized by process 100. In any event, applicable washing factors or parameters used to govern a wash cycle may be programmed into machine 111 (for example, via an appropriate user interface, control panel, or the like), and may then be initiated for each wash load or batch.

Once the wash cycle is completed, machine 111 may be emptied on the sterile side, and garment 101 (along with the rest of a batch with which garment 101 is associated) may be subjected to a suitable drying cycle (reference numeral 120). In that regard, drying cycle 120 may employ any of various types of commercially available driers, one of which is depicted at reference numeral 121 in FIG. 1. Drier 121 may be embodied in or comprise an ultra-low particulate air (ULPA) filtered steam heated dryer or another apparatus having operating characteristics that are appropriate for the particular process 100 being implemented (which, as noted above, may vary from application to application or be selected as a function of, or otherwise influenced by, the nature of garment 101 to be sterilized). As with washing machine 111, the present disclosure is not intended to be limited by the particular drier 121 employed in process 100, though it is noted that for most commercial applications, it is desirable that all parts of the equipment that get wet (for example, the wash and dry cylinders in machine 111 and drier 121, respectively) be compatible with use of deionized water; stainless steel, plastic, and certain glasses or laminated materials may be suitable for this purpose.

Upon inspection (reference numeral 130) to ensure appropriate cleaning and drying, garment 101 or other items may be packaged and sealed (reference numeral 140) for further processing. It is noted that the operations depicted at stations 130 and 140 may include human intervention or action on the part of a facility worker or administrator, for example, but they may also be executed autonomously or automatically, for instance, by commercially available equipment designed for such purposes. For example, inspection 130 may comprise examination by a person, by optical scanners or machine vision apparatus (operative in the visible spectrum or at wavelengths above or below the visible spectrum), or by a combination of these. Similarly, packaging and sealing at 140 may be performed manually in some instances, or may be fully automated in other instances, depending, for example, upon the nature and desired throughput of process 100, expenses associated with such automated industrial equipment, sterilization or cross-contamination concerns, or a combination of these and a variety of other factors.

At packaging and sealing station 140, clean and dry garment 101 or other items are inserted into and sealed within a breather bag 141 for further processing. In many applications, breather bag 141 may be constructed of polyethylene, paper, or olefin material (such as TYVEK™), though it is noted that other materials generally known in the art may have utility in maintaining sterility of garment 101; these may be selected as a function of the level of sterility desired, the expected environment and handling processes to which breather bag 141 may be subjected in downstream processing or shipping, and other factors that are application-specific. Whether performed by an operator or by a machine, the operations at 140 result in garment 101 being inserted into breather bag 141, and breather bag 141 being sealed (for example, in a conventional manner) at station 140. At this point, both garment 101 and breather bag 141 are sterile, as breather bag 141 has yet to leave the cleanroom environment of process 100.

Scanning or other inventory control (reference numeral 150) may be performed prior to packaging of breather bag 141 into a bin (reference numeral 160) for shipping. Inventory control 150 may utilize the aforementioned unique reference number or other identifier associated with garment 101 such that each garment 101 in process 100 may be tracked and monitored during downstream processing operations. In some implementations, bar code readers, optical scanners, or machine vision technologies may be employed, for instance, to read or otherwise to acquire such a reference number or identifier, such that the specific contents of each breather bag 141 are known prior to packaging at the operation depicted at reference numeral 160. In FIG. 1, an optical scanner and computer are illustrated at reference numeral 151, but those of skill in the art will appreciate that any of various types of inventory monitor and control hardware and software implementations may be used for this purpose.

Once identified and logged or otherwise recorded in an inventory monitor and control database or other software application, one or more breather bags 141 may be placed into a bin (one of which is identified by reference numeral 161 in FIG. 1) for transport or shipping. Prior to leaving the cleanroom environment, bin 161 may be sealed in a conventional manner to prevent contamination of breather bag 141, but there is no way to guaranty that the seal will not break or that bin 161 will not otherwise be breached following its exit from the sterile environment.

Once garment 101 or other item is clean and dry, as set forth above, it may be rendered sterile via a terminal sterilization process. In a typical commercial implementation, such terminal sterilization occurs following shipping (reference numeral 170 in FIG. 1) due to the fact that the outside of breather bag 141 is exposed to unsterile environments after it leaves the cleanroom environment of process 100. In some situations, $^{60}$CO gamma irradiation, high temperature ethylene oxide, or both, may be employed via a process validated to International Organization for Standardization (ISO) 11137 to ensure sterility of garments (such as garment 101) or other items to a required or desired Sterility Assurance Level. As noted above, however, this terminal sterilization must generally occur after shipping 170, when garment 101 reaches its destination, putting a burden on the customer of the facility executing process 100.

In a departure from conventional technologies, a validation of terminal sterility process (reference numeral 190 in FIG. 1) may be inserted into the methodology of process 100 to ensure that the packaging around breather bag 141 remains sterile after leaving the cleanroom environment. This validation process is illustrated in more detail in FIG. 2.

In particular, FIG. 2 is a simplified process flow diagram illustrating aspects of a method of validating sterilization of a garment, which aspects may be inserted into the process flow depicted in FIG. 1.

As illustrated in FIG. 2, a method of terminal sterilization 190 may begin (block 191) with identifying items to be sealed in a tote liner (illustrated in FIG. 3). As indicated in FIG. 2, the packing process at 191 may involve sealing breather bags 141 into a tote liner having a structure that is compatible with $CO_2$ sterilization as set forth herein, and it may be desirable in many applications first to identify, record, catalog, or otherwise to memorialize the items (such as garment 101) in each breather bag 141 that gets loaded in a particular tote liner. In that regard, the inventory control procedures executed at station 150 in FIG. 1 may be leveraged at block 191 to determine and to record the contents of each tote liner that is loaded with breather bags 141, as the contents of each breather bag 141 may already have been determined and recorded (at block 150).

Specifically, in operation of terminal sterilization process 190, one or more breather bags 141 (that have previously been loaded with sterilized items, such as a garment 101, at block 140 in FIG. 1) may be identified (such as by a bar code or other indicia, similar to the operation described above with reference to block 150 in FIG. 1) for inventory monitoring and control purposes. Once sealed within a suitable tote liner at block 191, the breather bags 141 and their respective contents are prepared for terminal sterilization.

As indicated at block 217, a validation or other determination may be made to confirm, for example, the number of items (such as garments 101) in each tote liner, or the number of tote liners to be subjected to a particular cleaning cycle, which may be specific to a particular terminal sterilization process 190 (i.e., application-specific). This validation or confirmation at block 217 may employ the inventory monitor and control data acquired at blocks 150 and 191, for example, and may be used to set operational parameters for downstream processing. For example, where all the breather bags 141 in a particular tote liner contain a certain type of item for a certain type of expected use, the cleaning cycle at 192 (described below) may utilize certain parameters that may differ from those utilized for different types of items or different required or desired Sterility Assurance Levels. Specifically, the volume and nature of the items identified at block 217 may govern or otherwise influence certain cleaning parameters such as temperature, pressure, duration, concentration of cleaning solutions, and the like. In some implementations when process 190 is intended to be used for a particular batch size (i.e., the same number and type of items) at every cleaning cycle, the operations at block 217 may be omitted, for instance, or may be simplified only to determine whether a cleaning apparatus will be overloaded with a particular batch.

With respect to the tote liner itself, it is noted that one implementation may generally comprise a $CO_2$ permeable sleeve (such as a bag, for instance), the sleeve allowing liquid $CO_2$ and a sterilant to permeate a material of the sleeve during a pressurized cleaning cycle (block 192, described below); and a biological indicator to indicate a level of sterility to at least a Sterility Assurance Level of $10^{-6}$. The biological indicator may be contained in an interior space within the sleeve, for example, or integrated into a structure (such as a pocket or recess) of the sleeve. In operation, the biological indicator may provide an indication of the Sterility Assurance Level of the breather bags 141 inside the tote liner, so it may generally be desirable to expose the biological indicator to the same environmental conditions as those experienced by the breather bags 141 (i.e., to deploy the biological indicator inside the tote liner or otherwise to integrate the biological indicator with the structure of the sleeve of the tote liner).

The sleeve of the tote liner may be so sized and dimensioned to accommodate one or more breather bags 141 containing one or more sterilized items, such as garment 101 or other items, and may include a sealing mechanism to prevent contamination of the breather bags 141 contained within the sleeve. In some implementations, the sealing mechanism may be embodied in or comprise a cleanroom compatible coil zipper designed to maintain sterility of the breather bag 141 inside the sleeve, though it is noted that the sealing process at block 191 may be facilitated by activation or execution of any of various sealing mechanisms or processes generally known in the art. Some such sealing paradigms are described in U.S. Pat. No. 10,183,090, but the present disclosure is not intended to be limited by any particular process, mechanism, or methodology use to seal a tote liner at block 191.

In some terminal sterility applications such as that depicted in process 190, the sterilant used for cleaning may be embodied in or comprise a solution comprising between 15% and 30% weight to volume of hydrogen peroxide; other concentrations are contemplated. It will be appreciated that the sleeve may be constructed of a material to allow the cleaning solution (along with liquid $CO_2$) to permeate into the interior of the sleeve to sterilize the breather bags 141 and the biological indicator, and so the material used to construct the sleeve of the tote liner may be selected as a function of permeability, either independently or in combination with a variety of other factors such as cost, durability, weight, and the like, as a design choice and in accordance with the expected cleaning parameters anticipated or desired at block 192.

The terminal sterilization process 190 may proceed with a cleaning cycle as indicated at block 192. Such a cycle may proceed for a duration of between about 15 minutes and about 40 minutes, depending upon a variety of factors. In some implementations, the cleaning cycle at block 192 is a high pressure, low temperature cleaning cycle. It will be appreciated that the terms "high pressure" and "low temperature" are relative, and may be application-specific. In accordance with one aspect of the disclosed subject matter, as noted above, the cleaning cycle at block 192 may employ liquid $CO_2$ and a sterilant (such as a solution containing hydrogen peroxide). The pressure and temperature of cleaning cycle 192 may be inter-dependent, for example, and may additionally be dictated or influenced by the concentration of the hydrogen peroxide cleaning solution, the capabilities and operational characteristics of the machine used for the cleaning cycle, and a variety of other factors.

For instance, while a relatively high pressure may be required to maintain $CO_2$ in a liquid state, it is noted that the pressure necessary for this is generally temperature dependent. In the context of the present disclosure, the term "high pressure" is generally meant to indicate a pressure in the range of between about 250 pounds per square inch (psi) and about 1000 psi, though in some applications, a range of about 500 psi to about 750 psi will be appropriate, depending upon the temperature of the cleaning cycle at block 192. Similarly, in this context, the term "low temperature" is intended to mean a temperature in the range of about 0° Celsius to about 40° Celsius, though in some applications, a range of about 15° Celsius to about 30° Celsius will be appropriate, depending upon the pressure of the cleaning cycle. In accordance with this aspect of the disclosed subject matter, some cleaning cycles at block 192 may use temperatures and pressures within the foregoing ranges to maintain the $CO_2$ in the wash cylinder of the machine in a liquid state.

In that regard, temperature and pressure parameters may be influenced by the capabilities or operational characteristics of the machine used for the cleaning cycle at block 192. As with machine 111 described above with reference to FIG. 1, the cleaning cycle operation depicted at reference numeral 192 may be performed in any of various commercially available washing machines that typically employ a cylinder to accommodate tote liners or other objects to be cleaned. The cylinder of the machine may be designed and capable of operating within the boundary conditions set forth herein (i.e., pressures of between about 250 psi and about 1000 psi, and temperatures of about 0° Celsius to about 40° Celsius) to accommodate liquid $CO_2$ and to withstand exposure to the cleaning solution comprising the sterilant. Where a particular machine's wash cylinder can accommodate very high pressures, the temperature tolerance may be the less important factor; where the machine's wash cylinder can withstand very low temperatures, the pressure tolerance may be the less important factor.

Those of skill in the art will appreciate that the cleaning cycle at block 192 may be implemented or executed by any suitable type or model of washing machine generally known in the art (either "off the shelf" or modified with appropriate pumps to maintain pressure or inlets to accept $CO_2$ and a sterilant solution) provided that the foregoing temperature and pressure ranges are within tolerances of the wash cylinder in which the cleaning cycle 192 occurs. The present disclosure is not intended to be limited by any particular manufacturer, model, type, or specific operational characteristics of the machine that executes the operations depicted at block 192, though it is noted that an appropriate inlet or inlets (e.g., for injection of $CO_2$ and a sterilant solution) may be desired for the process 190 set forth herein, depending upon the construction of the machine executing the cleaning cycle at block 192.

It will also be appreciated that the duration of the cleaning cycle at block 192 may depend upon the foregoing and other factors. While a range of between about 15 minutes and about 40 minutes is depicted in FIG. 2, other durations (e.g., shorter than 15 minutes or longer than 40 minutes) may be suitable, depending upon other parameters used for the cleaning cycle. For instance, a lower temperature of the cleaning cycle may result in sterilization more slowly than may occur at a higher temperature, or a higher pressure may result in faster permeation of the liquid $CO_2$ and sterilant solution through the structure of the sleeve of the tote liner, resulting in faster sterilization. The duration of the cleaning cycle may also depend upon the concentration of the sterilant solution supplied to the wash cylinder, the overall volume of the wash cylinder, the overall volume of the breather bags 141 in a particular batch, or a combination of these and other factors.

In that regard, a mixture of $CO_2$ and a sterilant solution may be supplied to the wash cylinder of the machine executing the cleaning cycle as depicted in block 199. In some applications noted above, the sterilant may be embodied in or comprise a solution comprising between about 15% and about 30% weight to volume of hydrogen peroxide to water. A weight to volume ratio of approximately 30% hydrogen peroxide to water is generally consider to be the maximum ratio that will not render the hydrogen peroxide volatile, and it is desirable in some cleaning applications to get as close to this 30% ratio as is possible, as this represents about the most pure form of hydrogen peroxide as is commercially practicable. In the event that this ratio moves lower in the range from 30% closer to 15%, it may be desirable to increase the duration of the cleaning cycle 192, or to adjust the temperature or pressure parameters inside the wash cylinder executing the cleaning cycle, or both, to achieve the Sterility Assurance Level desired in cleaning cycle 192. In any event, concentrations of less than 15% weight to volume of hydrogen peroxide to water may be employed, though other parameters may be adjusted to compensate for these lower concentrations. While it is not expected that higher concentrations (e.g., above about 30% weight to volume of hydrogen peroxide to water) will be usable in the context of process 190, it is noted that other sterilants are contemplated. In operation, any sterilant that is compatible with liquid $CO_2$ and that is capable of permeating the material used for the sleeve of the tote liner, may be injected into the cleaning cycle as depicted at block 199.

The efficacy of the cleaning cycle (block 192) may be observed or validated as indicated at block 198. Specifically, it may be desirable not to terminate the cleaning cycle at block 192 unless and until it is determined (at block 198) that the necessary or desired Sterility Assurance Level has been achieved. In that regard, as noted above, the duration of the cleaning cycle at block 192 may range between about 7 minutes and about 60 minutes or longer, depending upon the duration that is necessary or desired to achieve sterility in a particular application. This validation or determination may involve or comprise examination or observation of a biological indicator by a person, by optical scanners or machine vision apparatus (operative in the visible spectrum or at wavelengths above or below the visible spectrum), or by a combination of these. As is typical, and as the term implies, a biological indicator may provide an indication that the biological material incorporated into or attendant therewith has been sterilized. This indication may be in the form of a color change of a patch of material or some other indicum of sterilization; in that regard, the validation or determination at block 198 may be dependent upon the nature or characteristics of the indication provided by the biological indicator. Where such an indication is susceptible of viewing, scanning, or other optical reading by an automated machine or process, then block 198 may be executed substantially autonomously or automatically by equipment suitably configured to accomplish this task; additionally or alternatively, the operations at block 198 may be performed substantially or exclusively by an operator or administrator of terminal sterility process 190. In either event, the dashed line between blocks 198 and 192 is intended to indicate that the validation or determination process at block 198 is optional. In some implementations, validation may be presumed based upon process parameters and the duration of the cleaning cycle 192 (e.g., that may be predetermined or dynamically adjusted as a function of the items subjected to the cleaning cycle, itself, the concentration of the solution used as the sterilant, the duration of the cleaning cycle, or a combination of these and other factors as noted above). In some implementations, the biological indicator may be provided with a wireless transmitter, beacon, or other electronic device to provide an electronic signal indicating a current Sterility Assurance Level. In such circumstances, signals received from the biological indicator (at block 198) may be used to terminate the cleaning cycle (at block 192) at an appropriate time or following determination of an appropriate Sterility Assurance Level.

Following the cleaning cycle (at block 192), a pressure inside the cylinder of the machine executing cleaning cycle 192 may be lowered as indicated at block 193. In many applications, it may be desirable to lower the pressure inside the cylinder at a rate that has been determined not to damage the biological indicator. For some applications, this operation may comprise lowering the pressure inside the wash cylinder at a rate of approximately 2 psi/sec to approximately 7 psi/sec, though it will be appreciated that this rate may depend upon the type of biological indicator used and the tolerances of the substrate or other structure on which the biological indicator is deployed.

In some applications requiring high Sterility Assurance Levels down to $10^{-6}$, the biological indicator may be embodied in or comprise *Bacillus atrophaeus*; with such a biological indicator, the above range of approximately 2 psi/sec to approximately 7 psi/sec may be adequate not to damage the biological material incorporated into or used in connection with the biological indicator, though those of skill in the art will appreciate that this may depend upon other cleaning cycle parameters such as overall pressures and temperatures to which the biological indicator and its substrate or other carrier medium or structure have been subjected. In some instances, for example, it may be desirable to restrict the pressure change to rate of approximately 3 psi/sec to approximately 5 psi/sec.

In operation, the goal of utilizing a biological indicator in the sterilization arts is to confirm that all biological organisms or other contaminants have been either killed or rendered harmless to design specifications, expectations, or requirements. *Bacillus atrophaeus* has been found to have utility in this regard, and the typical assumption in the sterilization industry is that if *Bacillus atrophaeus* (incorporated into or otherwise used in connection with a biological indicator) has been killed or otherwise rendered harmless (i.e., "neutralized"), then any other organisms and any other contaminants will have also been neutralized during cleaning process 192. In some implementations, other biological indicators may be employed, such as any of a variety of *Bacillus* sp. spores or other biologic material. The type and nature of the biologic material employed in the biological indicator is not as important as knowledge of the Sterility Assurance Level that such biological indicator is intended to assure, and the present disclosure is not intended to be limited to any particular biological indicator or biologic material used in connection therewith; these are design choices that may be influenced by other factors that drive process 190, agreements with customers of the facility executing process 100, or a combination of these and other factors.

In accordance with the disclosed subject matter, one aspect of the terminal sterilization process 190 may generally involve determining or ensuring that all such *Bacillus atrophaeus* (or other) organisms incorporated into or otherwise used in connection with a biological indicator have been neutralized by the cleaning cycle at 192 (and, ultimately, the entire terminal sterility process 190).

On the other hand, it is also important, as a practical matter, to ensure a recipient of sterilized items (such as garment 101) that the sterilization process has been successful. As a consequence, it may also be important to prove that the biological indicator itself has not been damaged or otherwise compromised. The operation at block 193 is intended to ensure that the biologic material used for the biological indicator has not been so damaged or compromised, and this may include ensuring that the substrate, carrier, or device incorporating such biologic material as the biological indicator, has also not been so damaged or compromised. Accordingly, it will be appreciated that the pressure reduction operation depicted at block 193 includes lowering a pressure inside the wash cylinder at a rate that not only preserves the biologic material used as the biological indicator (e.g., *Bacillus atrophaeus*), but also preserves the integrity of the substrate, carrier, or other device that is used to maintain the biological indicator. Accordingly, it is desirable to reduce the pressure in such a manner as not to damage the materials or the structure used in the biological indicator—a rate of about approximately 2 psi/sec to approximately 7 psi/sec will be appropriate for most applications with respect to known biological indictor embodiments.

The process 190 may continue with packing appropriately sterile tote liners into shipping containers (block 194). This process may be similar to that described above with reference to block 160 in FIG. 1, except that in this case, the tote liners containing breather bags 141 are loaded such that the exterior of each breather bag 141 may be certified as having been sterilized. In the event that a shipping container (such as depicted at reference numeral 161) is breached or is otherwise subjected to an unsterile environment, the integrity of the exterior of the breather bags 141 within the tote liner may still be validated and ensured.

Upon packing at block 194, tote liners may be shipped to third parties or other customers of the processing facility executing the process at 100 as indicated at block 170. Additional terminal sterility processing may not be needed upon receipt of the tote liner at the destination.

It is noted that the arrangement of the blocks and the order of operations depicted in FIG. 2 are not intended to exclude other alternatives or options. For example, the operations depicted at blocks 192, 198, and 199, or the operations depicted at blocks 191 and 217, may be made to occur substantially simultaneously in some implementations. Those of skill in the art will appreciate that the foregoing subject matter is susceptible of various design choices that may influence the order or arrangement of the operations depicted in FIG. 2.

FIG. 3 is a simplified block diagram illustrating aspects of a tote liner for use in connection with a sterilization process. In accordance with the present disclosure, tote liner 341 may generally comprise a sleeve 347 and a biological indicator 343. As noted above, sleeve 347 may generally be sized and dimensioned to receive one or more breather bags 141, and may be constructed of material that is $CO_2$ permeable, thus allowing liquid $CO_2$ and a sterilant solution to permeate a material of sleeve 347 during a pressurized cleaning cycle such as illustrated and described above with reference to block 192 in FIG. 2. Tote liner 341 may generally be fashioned in the form of a bag or other container having the containment and permeability functionality set forth herein.

The permeability aspects of the material used for sleeve 347 may be application specific, and may be selectively modified or otherwise adjusted as a function of the nature or concentration of the sterilant solution used in the cleaning cycle (see reference numerals 192 and 199 in FIG. 2), the capabilities of the wash cylinder used in connection with such cycle, the nature of the item (such as garment 101) to be terminally sterilized, or a combination of these and other factors.

Biological indicator 343 may be placed in or otherwise disposed within or in connection with sleeve 347. As noted above, biological indicator 343 may simply be placed in sleeve 347 along with breather bags 141, or it may be integrated with or into a structure of sleeve 347, such as within a cavity, pocket, or recess (reference numeral 342 in FIG. 3) integrated into the structure of sleeve 347. As noted above, any of various commercially available biological indicators 343 may be employed in process 190, and may be selected as a design choice, depending upon a variety of factors. The structure of sleeve 347 (and its constituent materials) selected for accommodating biological indicator 343 may vary, depending upon the nature and structural characteristics of the substrate or other structure supporting or carrying the biologic material of biological indicator 343, the conditions expected for the cleaning cycle 192, or a combination of these and other factors. For example, it may be desirable to fashion a recess, such as indicated at 342, to accommodate biological indicator 343 in an orientation that facilitates reading, scanning, or other observation of a visual indication of Sterility Assurance Level without necessitating re-orientation or other adjustment of a position of biological indicator 343 during use. In some implementations utilizing wireless near-field communications (NFC) such as Bluetooth™, radio frequency identification (RFID), or other wireless communications protocols, the specific orientation of biological indicator 343 within sleeve 347 or recess 342 may be of little to no importance.

As noted above, tote liner 341 may be fabricated in such a manner that biological indicator 343 is contained in an interior space within sleeve 347; or it may be fabricated in such a manner that biological indicator 343 is integrated into or accommodated within a structure (such as recess 342) of sleeve 347. In either event, breather bags 141 and biological indicator 343 may be sealed within sleeve 347 of tote liner 341 substantially as set forth above prior to terminal sterilization at cleaning cycle 192. This sealing process may involve implementation or activation of a sealing mechanism 349, which may include a cleanroom compatible coil zipper designed to maintain sterility of breather bag 141 inside sleeve 347, or some other mechanism.

Several features and aspects of a system and method have been illustrated and described in detail with reference to particular embodiments by way of example only, and not by way of limitation. Those of skill in the art will appreciate that alternative implementations and various modifications to the disclosed embodiments are within the scope and contemplation of the present disclosure. Therefore, it is intended that the present disclosure be considered as limited only by the scope of the appended claims.

What is claimed is:

1. A sterilization validation method comprising:
loading a sealed breather bag containing a cleaned item into a $CO_2$ compatible tote liner, the tote liner comprising a $CO_2$ permeable sleeve and containing a biological indicator to indicate a level of sterility;
sealing the tote liner and exposing the sealed tote liner to a cleaning cycle utilizing $CO_2$ and a sterilant;
lowering a pressure following the cleaning cycle slowly to prevent damage to the biological indicator; and
confirming sterilization using the biological indictor; and packaging the sterilized tote liner into a container for shipping.

2. The method of claim 1 wherein the cleaned item is one of equipment, an instrument, a garment, and material.

3. The method of claim 1 wherein the exposing comprises utilizing a solution comprising between 15% and 30% weight to volume of hydrogen peroxide as the sterilant.

4. The method of claim 1 wherein the exposing comprises utilizing a high pressure, low temperature cleaning cycle.

5. The method of claim 4 wherein the high pressure, low temperature cleaning cycle achieves a pressure of about 250 psi to about 1000 psi inside a wash cylinder of a machine configured to execute the cleaning cycle.

6. The method of claim 5 wherein the high pressure, low temperature cleaning cycle achieves a temperature of about 0° Celsius to about 40° Celsius inside the wash cylinder.

7. The method of claim 5 wherein the lowering comprises lowering the pressure inside the wash cylinder at a rate of approximately 2 psi/sec to approximately 7 psi/sec.

8. The method of claim 1 wherein the confirming comprises certifying that an exterior surface of the breather bag is sterile inside the tote liner.

9. The method of claim 8 wherein the confirming comprises certifying the level of sterility to at least a Sterility Assurance Level of $10^{-6}$.

10. The method of claim 9 wherein the biological indicator comprises *Bacillus Atrophaeus*.

11. A tote liner for use in a sterilization validation method, the tote liner comprising:
- a $CO_2$ permeable sleeve, the sleeve allowing liquid $CO_2$ and a sterilant to permeate a material of the sleeve during a pressurized cleaning cycle, wherein the sleeve is sized and dimensioned to accommodate a breather bag containing a sterilized item; and
- a biological indicator to indicate a level of sterility to at least a Sterility Assurance Level of $10^{-6}$, wherein the biological indicator comprises *Bacillus Atrophaeus*; and
- a sealing mechanism to prevent contamination of the breather bag, the sealing mechanism comprising a cleanroom compatible coil zipper designed to maintain sterility of the breather bag inside the sleeve.

12. The tote liner of claim 11 wherein the biological indicator is contained in an interior space within the sleeve.

13. The tote liner of claim 11 wherein the biological indicator is integrated into a structure of the sleeve.

14. The tote liner of claim 11 wherein the sterilant comprises a solution comprising between 15% and 30% weight to volume of hydrogen peroxide and wherein the sleeve is constructed of a material to allow the solution to permeate.

15. A tote liner for use in a sterilization validation method, the tote liner comprising:
- a CO2 permeable sleeve, the sleeve allowing liquid CO2 and a sterilant to permeate a material of the sleeve during a pressurized cleaning cycle, wherein the sleeve is sized and dimensioned to accommodate a breather bag containing a sterilized item;
- a biological indicator to indicate a level of sterility to at least a Sterility Assurance Level of 10-6; and
- a sealing mechanism to prevent contamination of the breather bag, the sealing mechanism comprising a cleanroom compatible coil zipper designed to maintain sterility of the breather bag inside the sleeve.

16. The tote liner of claim 15 wherein the biological indicator is contained in an interior space within the sleeve.

17. The tote liner of claim 15 wherein the biological indicator is integrated into a structure of the sleeve.

18. The tote liner of claim 15 wherein the sterilant comprises a solution comprising between 15% and 30% weight to volume of hydrogen peroxide and wherein the sleeve is constructed of a material to allow the solution to permeate.

* * * * *